(12) United States Patent
Repasi et al.

(10) Patent No.: US 8,664,397 B2
(45) Date of Patent: Mar. 4, 2014

(54) PYRROLOPYRIDINE-2-CARBOXYLIC ACID AMIDE DERIVATIVE USEFUL AS INHIBITOR OF GLYCOGEN PHOSPHORYLASE

(75) Inventors: Jozsef Repasi, Budapest (HU); Andras Szabo, Budapest (HU)

(73) Assignee: Prosidion Limited, Oxford (GB)

( * ) Notice: Subject to any disclaimer, the term of this patent is extended or adjusted under 35 U.S.C. 154(b) by 886 days.

(21) Appl. No.: 11/792,183

(22) PCT Filed: Dec. 2, 2005

(86) PCT No.: PCT/GB2005/050234
§ 371 (c)(1),
(2), (4) Date: Jun. 20, 2008

(87) PCT Pub. No.: WO2006/059165
PCT Pub. Date: Jun. 8, 2006

(65) Prior Publication Data
US 2008/0293761 A1    Nov. 27, 2008

Related U.S. Application Data

(60) Provisional application No. 60/632,463, filed on Dec. 2, 2004.

(51) Int. Cl.
*C07D 471/02* (2006.01)
(52) U.S. Cl.
USPC .......................................... 546/113

(58) Field of Classification Search
USPC .......................................... 546/113
See application file for complete search history.

(56) References Cited

U.S. PATENT DOCUMENTS 7,405,210 B2 * 7/2008 Bradley et al. ............. 514/231.5

FOREIGN PATENT DOCUMENTS

| WO | WO-0220530 A1 | 3/2002 |
| WO | WO 2004104001 | * 12/2004 |
| WO | WO-2004104001 A2 | 12/2004 |

OTHER PUBLICATIONS

Somsak et al. Current Pharmaceutical Design, 2003, 9, 1177-1189.*
Zubrick, Organic Chem Lab Survival Manual. John Wiley &Sons, Inc. 1988.*
Montalbetti et al. Tetrahedron 61 (2005) 10827-10852.*

* cited by examiner

*Primary Examiner* — Nizal Chandrakumar
(74) *Attorney, Agent, or Firm* — Mintz Levin Cohn Ferris Glovsky and Popeo, P.C.; Heidi A. Erlacher; Shovon Ashraf

(57) ABSTRACT

The present invention is directed to a novel form of a pyrrolopyridine-2-carboxylic acid amide of formula (I), which is an inhibitor of glycogen phosphorylase, compositions containing it and their use in therapy. The invention is also directed to processes for production of the novel form, novel intermediates used in said processes and processes for the production of said intermediates.

9 Claims, 6 Drawing Sheets

PYRROLOPYRIDINE-2-CARBOXYLIC ACID AMIDE DERIVATIVE USEFUL AS INHIBITOR OF GLYCOGEN PHOSPHORYLASE

RELATED APPLICATIONS

This application is a national stage application, filed under 35 U.S.C. §371, of International Application No. PCT/GB05/50234, filed Dec. 2, 2005, which claims benefit of priority from U.S. Provisional Application No. 60/632,463, filed Dec. 2, 2004.

BACKGROUND OF THE INVENTION

The present invention is directed to a novel form of a pyrrolopyridine-2-carboxylic acid amide, which is an inhibitor of glycogen phosphorylase, compositions containing it and their use in therapy. The invention is also directed to processes for production of the novel form, novel intermediates used in said processes and processes for the production of said intermediates.

Inhibitors of glycogen phosphorylase are useful in the treatment of diabetes, hyperglycemia, hypercholesterolemia, hyperinsulinemia, hyperlipidemia, atherosclerosis or myocardial ischemia.

International Patent Application No. PCT/US2004/016243 (published after the priority date of the present invention) discloses pyrrolopyridine-2-carboxylic acid amide inhibitors of glycogen phosphorylase, including the compound 5-chloro-1H-pyrrolo[2,3-c]pyridine-2-carboxylic acid [1-(S)-(4-fluorobenzyl)-2-(4-hydroxypiperidin-1-yl)-2-oxoethyl]amide.

PCT/US2004/016243 describes the synthesis of 5-chloro-1H-pyrrolo[2,3-c]pyridine-2-carboxylic acid [1-(S)-(4-fluorobenzyl)-2-(4-hydroxypiperidin-1-yl)-2-oxoethyl]amide as the free base by amide coupling of either 2-(S)-[(5-chloro-1H-pyrrolo[2,3-c]pyridine-2-carbonyl)amino]-3-(4-fluorophenyl)propionic acid and 4-hydroxypiperidine or 5-chloro-1H-pyrrolo[2,3-c]pyridine-2-carboxylic acid and 2-(S)-amino-3-(4-fluorophenyl)-1-(4-hydroxypiperidin-1-yl)propan-1-one hydrochloride in dimethylformamide in the presence of diisopropylethylamine.

It is desirable to obtain novel forms of this compound having advantageous pharmacological properties and to provide improved processes for the production of such compounds.

SUMMARY OF THE INVENTION

5-Chloro-1H-pyrrolo[2,3-c]pyridine-2-carboxylic acid [1-(S)-(4-fluorobenzyl)-2-(4-hydroxypiperidin-1-yl)-2-oxoethyl]amide hydrochloride, which is an inhibitor of glycogen phosphorylase, is useful in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia, and as a cardioprotectant. There are also provided processes for its production.

DETAILED DESCRIPTION OF THE INVENTION

The present invention provides a compound which is a hydrochloride salt of 5-chloro-1H-pyrrolo[2,3-c]pyridine-2-carboxylic acid [1-(S)-(4-fluorobenzyl)-2-(4-hydroxypiperidin-1-yl)-2-oxoethyl]amide.

In the following, 5-chloro-1H-pyrrolo[2,3-c]pyridine-2-carboxylic acid [1-(S)-(4-fluorobenzyl)-2-(4-hydroxypiperidin-1-yl)-2-oxoethyl]amide may be referred to as the compound of Formula (I):

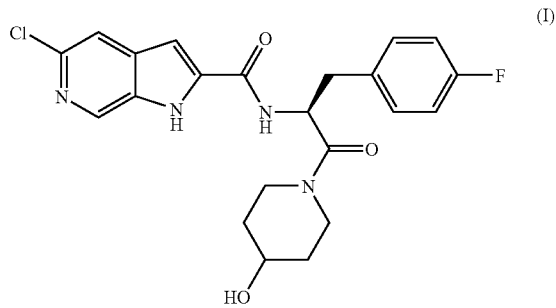 [SMILES: O=C(N[C@@H](Cc1ccc(F)cc1)C(=O)N1CCC(O)CC1)c1cc2cc(Cl)ncc2[nH]1]

and accordingly the compound of the invention is a hydrochloride of the compound of Formula (I).

The hydrochloride of the compound of Formula (I) is preferably in crystalline form. The hydrochloride of the compound of Formula (I) may also be amorphous.

The invention also embraces solvates of the hydrochloride of the compound of Formula (I). Solvates include complexes of the hydrochloride of the compound of Formula (I) with physiologically acceptable solvents, and refers in particular to hydrates.

The hydrochloride of the compound of Formula (I) may contain up to about 15% w/w of water. When the hydrochloride of the compound of Formula (I) is a hydrate it preferably comprises from 5 to 15% w/w, e.g. 10 to 15% w/w, of water.

The hydrochloride of the compound of Formula (I) may be an anhydrate.

The polymorphic form of the hydrochloride of the compound of Formula (I) may be identified by its characteristic X-ray powder diffraction pattern.

A form of the hydrochloride is shown in FIGS. 2-5 and exhibits characteristic peaks in the X-ray diffraction pattern. A further form of the hydrochloride is shown in FIG. 6 and also exhibits characteristic peaks in the X-ray diffraction pattern. A characteristic peak is one which has a relative intensity above 10% of the largest peak in the powdered XRD pattern. Any one of these peaks alone, or in combination, may be used to identify the form of the hydrochloride.

In addition to these characteristic peaks, FIGS. 2-5 and FIG. 6 show other minor peaks not reaching the 10% threshold in all samples. The intensity of these peaks vary with the particular orientation of the polymorph. These additional peaks may be used to confirm the presence of these forms of the hydrochloride, but their absence should not be used to determine that the particular material is not the hydrochloride.

As is readily apparent to one skilled in the art, the results of any X-ray powder diffraction may vary. This variance can be due to test sample preparation, the particular model of X-ray diffractometer used, the operator's technique, etc. The term "approximately" if used in defining a position of a characteristic peak in an X-ray powder diffraction pattern is defined as the stated 2θ value ±0.2°2θ.

The invention also provides a pharmaceutical composition comprising a hydrochloride of the compound of Formula (I), in admixture with a pharmaceutically acceptable carrier.

The invention also provides a pharmaceutical composition for the treatment of disease by inhibiting glycogen phosphorylase, resulting in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia comprising a pharmaceutically acceptable carrier and a non-toxic therapeutically effective amount of a hydrochloride of the compound of Formula (I).

Since the hydrochloride of the compound of Formula (I) is intended for pharmaceutical use it is preferably provided in substantially pure form, for example at least 60% pure, more suitably at least 75% pure especially at least 98% pure (% are on a weight for weight basis).

The pharmaceutical compositions of the invention comprise a hydrochloride of the compound of Formula (I) as an active ingredient, a pharmaceutically acceptable carrier and optionally other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The compositions are preferably suitable for oral administration. The pharmaceutical compositions may be conveniently presented in unit dosage form and prepared by any of the methods well known in the art of pharmacy.

In practice, the hydrochloride of the compound of Formula (I) can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the hydrochloride of the compound of Formula (I) may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The hydrochloride of the compound of Formula (I) can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each sachet or capsule preferably contains from about 0.05 mg to about 5 g of the active ingredient.

For example, a formulation intended for oral administration to humans may contain from about 0.5 mg to about 5 g of active agent, compounded with an appropriate and convenient amount of carrier material, which may vary from about 5 to about 95% of the total composition. Unit dosage forms will generally contain from about 1 mg to about 2 g of the active ingredient, typically 25 mg, 50 mg, 10 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a hydrochloride of the compound of Formula (I), or a pharmaceutically acceptable salt thereof, via conventional processing methods. As an example, a cream or ointment is prepared by admixing hydrophilic material and water, together with about 5% w/w to about 10% w/w of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a hydrochloride of the compound of Formula (I), or a pharmaceutically acceptable salt thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, diabetes and hyperglycemia may be effectively treated by the administration of from about 0.01 to 50 mg of a hydrochloride of the compound of Formula (I) per kilogram of body weight per day, or alternatively about 0.5 mg to about 3.5 g per patient per day. Similarly, hypercholesterolemia, hyperinsulinemia, hyperlipidemia, hypertension, atherosclerosis or tissue ischemia e.g. myocardial ischemia may be effectively treated by the administration of from about 0.01 to 50 mg of a hydrochloride of the compound of Formula (I) per kilogram of body weight per day, or alternatively about 0.5 mg to about 3.5 g per patient per day, e.g. 50 mg to 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The hydrochloride of the compound of Formula (I) may be used in the treatment of diseases or conditions in which glycogen phosphorylase plays a role.

Thus the invention also provides a method for the treatment of a disease or condition in which glycogen phosphorylase plays a role comprising a step of administering to a subject in need thereof an effective amount of a hydrochloride of the compound of Formula (I).

Diseases or conditions in which glycogen phosphorylase plays a role include diabetes (including Type I and Type II, impaired glucose tolerance, insulin resistance and diabetic complications such as neuropathy, nephropathy, retinopathy and cataracts), hyperglycemia, hypercholesterolemia, hyperinsulinemia, hyperlipidemia, hypertension, atherosclerosis, tissue ischemia e.g. myocardial ischemia.

The invention also provides a method for the treatment of hyperglycemia or diabetes comprising a step of administering to a subject in need thereof an effective amount of a hydrochloride of the compound of Formula (I).

The invention also provides a method for the prevention of diabetes in a human demonstrating pro-diabetic hyperglycemia or impaired glucose tolerance comprising a step of administering to a subject in need thereof an effective prophylactic amount of a hydrochloride of the compound of Formula (I).

The invention also provides a method for the treatment of hypercholesterolemia, hyperinsulinemia, hyperlipidemia, hypertension, atherosclerosis or tissue ischemia comprising a step of administering to a patient in need thereof an effective amount of a hydrochloride of the compound of Formula (I).

The invention also provides a method of cardioprotection e.g. following reperfusion injury, comprising a step of administering to a subject in need thereof an effective amount of a hydrochloride of the compound of Formula (I).

The invention also provides the use of a hydrochloride of the compound of Formula (I) in the treatment of a condition as defined above.

The invention also provides the use of a hydrochloride of the compound of Formula (I) in the manufacture of a medicament for the treatment of a condition as defined above.

The invention also provides a hydrochloride of the compound of Formula (I) for use in the treatment of a condition as defined above.

In the methods and uses of the invention the term "treatment" includes both therapeutic and prophylactic treatment.

The hydrochloride of the compound of formula (I) may, particularly for the treatment of type II diabetes, be administered to a patient at night time, e.g. at bed time and preferably after the patient has consumed their last meal of the day such that inhibition of glycogen phosphorylase occurs during the fasting period.

The hydrochloride of the compound of Formula (I) may be administered alone or in combination with one or more other therapeutically active compounds. The other therapeutically active compounds may be for the treatment of the same disease or condition as the hydrochloride of the compound of Formula (I) or a different disease or condition. The therapeutically active compounds may be administered simultaneously, sequentially or separately.

The hydrochloride of the compound of Formula (I) may be administered as polypharmacy with other active compounds for the treatment of diabetes, for example PPAR agonists, biguanides, sulfonylureas and other insulin secretagogues, insulin sensitisers, alpha-glucosidase inhibitors, dipeptidyl peptidase IV inhibitors, glucokinase activators, GLP-1 and GLP-1 analogues, insulin, insulin analogues, $\alpha 2$ agonists, fatty acid oxidation inhibitors, $\alpha$-glucosidase inhibitors, $\beta$-agonists, phosphodiesterase inhibitors, lipid lowering agents, antiobesity agents, amylin antagonists, lipoxygenase inhibitors, somostatin analogs, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, CRF antagonists and CRF binding proteins. The hydrochloride of the compound of Formula (I) may also be administered in combination with thyromimetic compounds, aldose reductase inhibitors, glucocorticoid receptor antagonists, NHE-1 inhibitors or sorbitol dehydrogenase inhibitors. These additional agents may be formulated and administered by methods known to those skilled in the art.

The hydrochloride of the compound of Formula (I) may exhibit advantageous properties compared to known glycogen phosphorylase inhibitors, for example, the solid compound exhibits improved handling properties which make it easier to isolate and formulate than known forms of the compound of Formula (I). The isolation of the hydrochloride salt of the compound of Formula (I) is improved both chemically and enantiomerically relative to the free base. In crystalline form the hydrochloride of the compound of Formula (I) also exhibits advantageous properties desirable for pharmaceutical active ingredients.

A hydrochloride of the compound of Formula (I) may be prepared, for example, by treating a compound of Formula (I) with HCl. Suitable conditions include dissolution of the compound of Formula (I) in an alcoholic solvent, e.g. methanol, ethanol or propanol, followed by the addition of hydrochloric acid e.g. 2M hydrochloric acid, and the subsequent removal of the solvent under reduced pressure.

A compound of Formula (I), 5-chloro-1H-pyrrolo[2,3-c]pyridine-2-carboxylic acid [1-(S)-(4-fluorobenzyl)-2-(4-hydroxypiperidin-1-yl)-2-oxoethyl]amide, may be prepared by the processes described in PCT/US2004/016243.

Accordingly, in a first process, the compound of Formula (I) may be prepared by coupling a compound of Formula (II), namely 5-chloro-1H-pyrrolo[2,3-c]pyridine-2-carboxylic acid, or a protected or activated derivative thereof, with an amine of Formula (III), namely 2-(S)-amino-3-(4-fluorophenyl)-1-(4-hydroxypiperidin-1-yl)propan-1-one hydrochloride, as shown in Scheme 1.

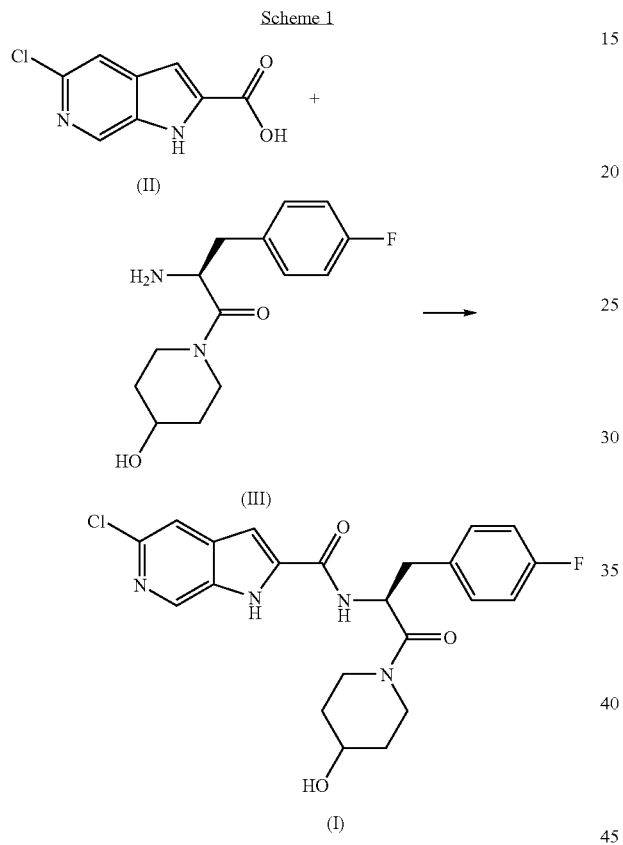

Typically, the compound of Formula (II), or a protected or activated derivative thereof, is combined with the compound of Formula (III) in the presence of a suitable coupling agent. Examples of suitable coupling reagents are 1-(3-dimethylaminopropyl)-3-ethylcarbodiimide hydrochloride/hydroxybenzotriazole (EDCI/HOBt), 1,1-carbonyldiimidazole (CDI), dicyclohexylcarbodiimide/hydroxybenzotriaole (DCC/HOBt), O-(1H-benzotriazol-1-yl)-N,N,N',N'-tetramethyluronium tetrafluoroborate (R. Knorr et al., *Tetrahedron Lett.*, 1989, 30, 1927-1930) and polymer supported carbodiimide-1-hydroxybenzotriazole (for representative procedures, see for example, Argonaut Technical Note 501 available from Argonaut Technologies, Inc., Foster City, Calif.). The couplings may be performed in an inert solvent, preferably an aprotic solvent at a temperature of about 0° C. to about 45° C. for about 1 to 72 h in the presence of a tertiary amine base such as diisopropylethylamine (DIPEA) or triethylamine. Exemplary solvents include acetonitrile, chloroform, dichloromethane, N,N-dimethylformamide (DMF) or mixtures thereof. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Thieme Verlag, 1974, Stuttgart, and M. Bodansky, Principles of Peptide Synthesis, Springer-Verlag, Berlin, 1984 and The Peptides, Analysis, Synthesis and Biology (Ed., E. Gross and J. Meienhofer), Vols 1-5, Academic Press NY 1979-1983.

The compound of Formula (II) can be obtained by the synthesis illustrated below in Scheme 2:

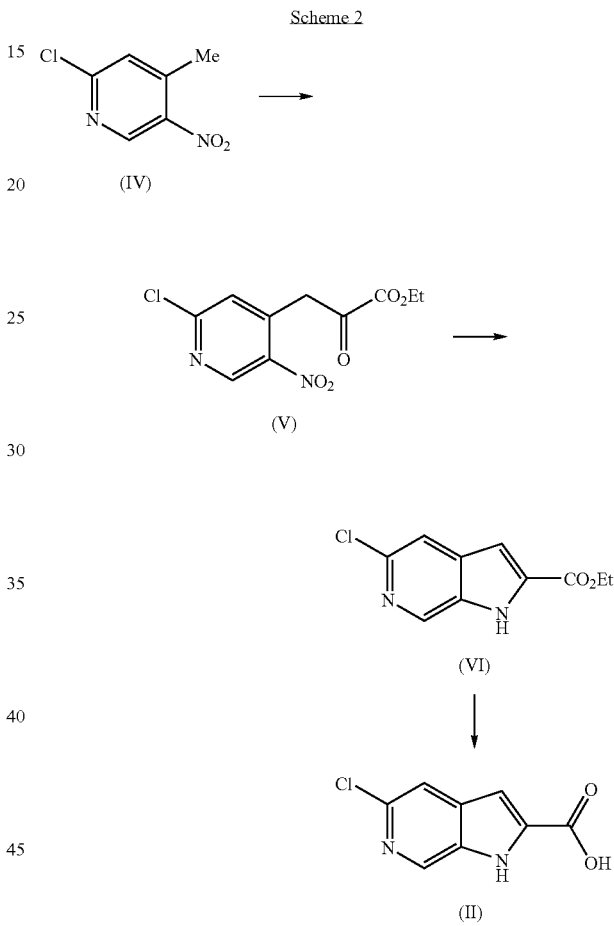

The compound of Formula (V) may be prepared by condensation of an ortho methyl nitro compound of Formula (IV) with an oxalate ester in a solvent such as diethyl ether in the presence of a base such as potassium ethoxide or DBU. The compound of Formula (VI) is prepared from a compound of Formula (V) under reducing conditions, such as iron powder and ammonium chloride, or by hydrogenation in ethanol using palladium catalysis. The compound of Formula (VI) undergoes ester hydrolysis using aqueous alkali to give the pyrrolopyridine-2-carboxylic acid of Formula (II). Further information on the conversion of the compound of Formula (IV) to the compound of Formula (II) is available in the literature (Kermack, et al., *J. Chem, Soc.*, 1921, 119, 1602; Cannon et al., *J. Med. Chem.*, 1981, 24, 238; Julian et al., in Heterocyclic Compounds, Vol 3 (Wiley, New York, N.Y., 1962, R. C. Elderfield, Ed.) p 18. The compound of Formula (IV) is available commercially.

Alternatively, the compound of Formula (II) can also be obtained by the synthesis in Scheme 3:

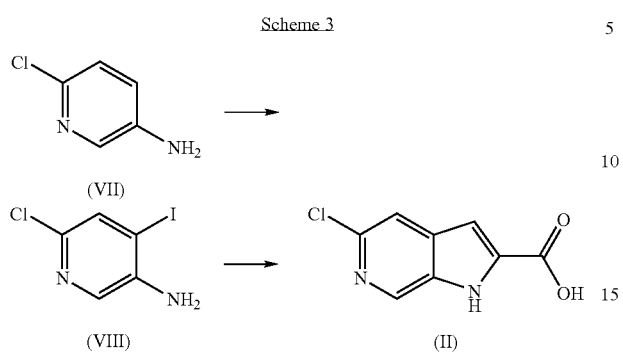

According to Scheme 3, the compound of Formula (II) is prepared by a Heck coupling of an ortho-iodo aminopyridine (VIII) followed by cyclisation at a temperature of between 100 to 150° C. in the presence of catalyst such as palladium acetate and a base such as DABCO in a solvent such as DMF (See Chen et al, J. Org. Chem. 1997, 62, 2676). The ortho-iodo aminopyridines (VIII) can be made by direct iodination of the aminopyridine (VII) using iodine in the presence of silver sulfate in a solvent such as ethanol at ambient temperature (see Sy, W., *Synth. Commun.*, 1992, 22, 3215). The compound of Formula (VII) is available commercially.

Alternatively the compound of Formula (VIII) for use in Scheme 3 may be prepared according to Scheme 4 by deprotection of an N-pivaloyl compound of Formula (X) by heating under reflux using hydrochloric acid. The N-pivaloyl compound of Formula (X) is in turn made by deprotonation of the compound of Formula (IX) with an organolithium such as tert-butyllithium in a suitable solvent such as THF, followed by quenching with iodine at a low temperature. The compound of Formula (IX) may be made by protection of the aminopyridine of Formula (VU) with trimethylacetyl chloride and a base such as triethylamine in a solvent such as dichloromethane.

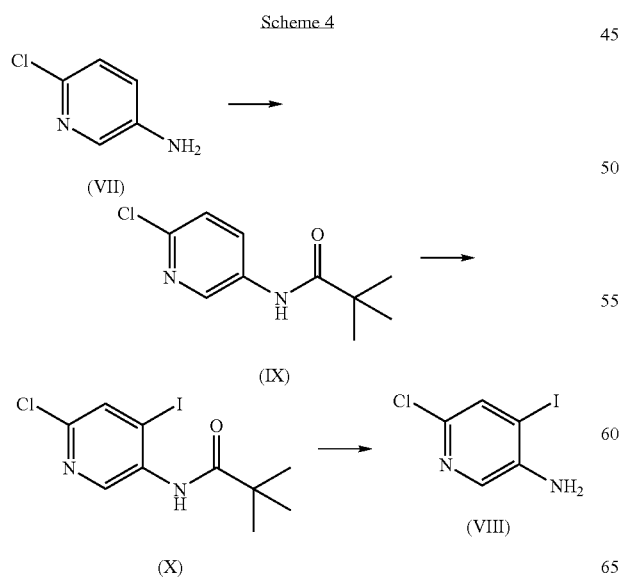

A further alternative for the preparation of a compound of Formula (VIII), shown in Scheme 5, is by the deprotection of an N-Boc protected compound of Formula (XII) using an acid such as trifluoroacetic acid in a solvent such as dichloromethane at ambient temperature. The N—BOC compound of Formula (XII) is in turn made by deprotonation of the compound of Formula (XI) with an organolithium such as n-butyllithium in the presence of N,N,N',N'-tetramethylethylenediamine (TMEDA) in a suitable solvent such as ether at temperatures around −70° C. followed by the addition of iodine at temperatures around −10° C. The N-Boc aminopyridine of Formula (XI) is routinely made from the aminopyridine of Formula (VU) using di-tert-butyldicarbonate by heating in a solvent such as 1,4-dioxane.

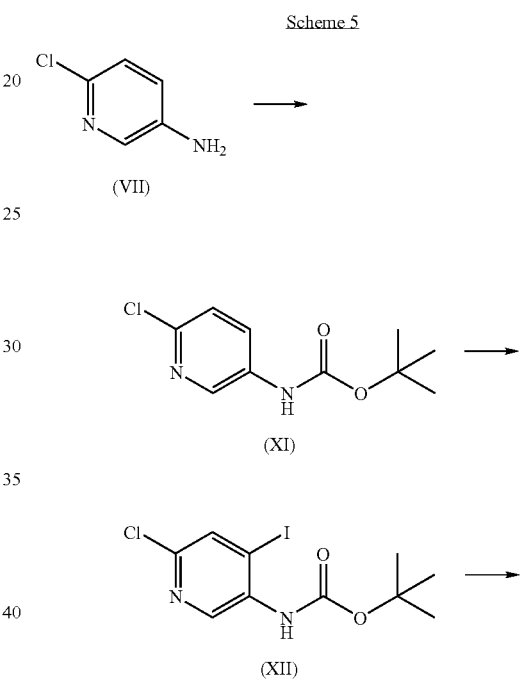

The compound of Formula (III) can be obtained by the synthesis described in Scheme 6 below:

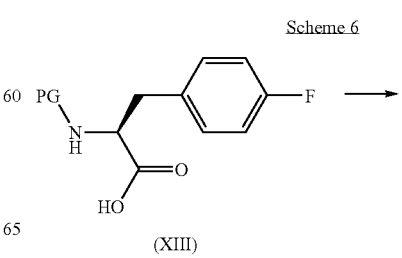

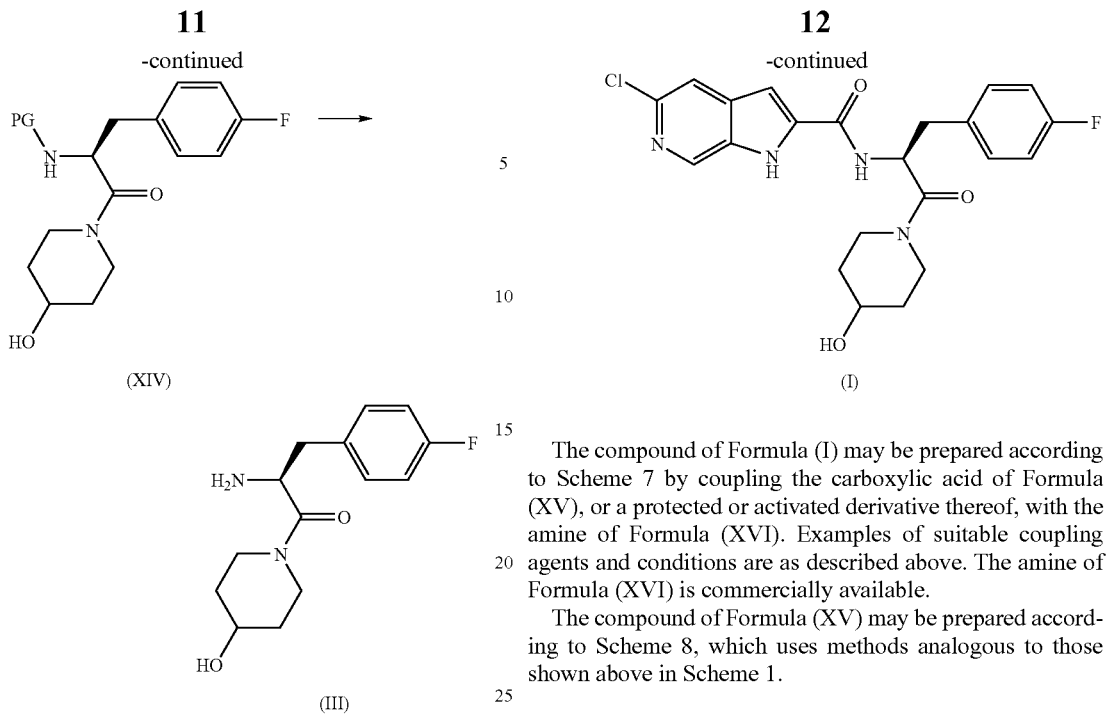

(XIV)

(III)

Compounds of Formula (XIII) are readily prepared by known techniques. PG represents a protecting group such as, for example, tert-butyloxycarbonyl (Boc). Compounds of Formula (XIV) are made from carboxylic acids of Formula (XIII) using standard coupling conditions, such as described above for Scheme 1.

The compound of Formula (III) may be prepared from compounds of Formula (XIV) by removal of the protecting group, where PG=Boc, under acidic conditions using for example trifluoroacetic acid in dichloromethane at temperatures of around 25° C.

A second process for the production of the compound of Formula (I) is illustrated in Scheme 7:

Scheme 7

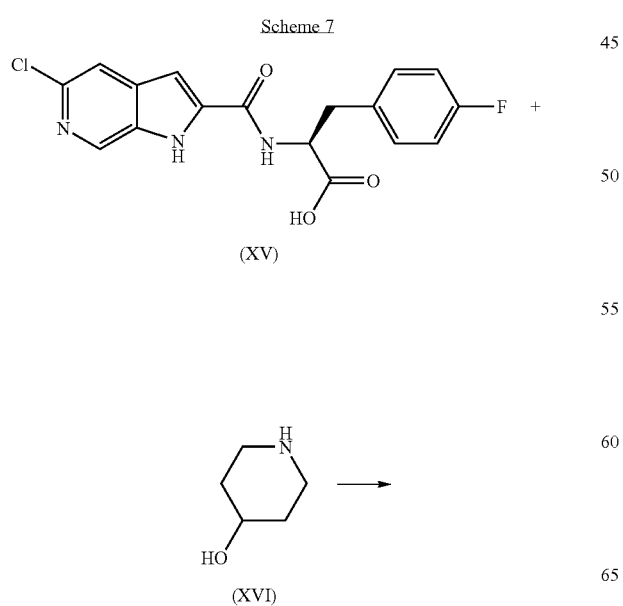

(I)

The compound of Formula (I) may be prepared according to Scheme 7 by coupling the carboxylic acid of Formula (XV), or a protected or activated derivative thereof, with the amine of Formula (XVI). Examples of suitable coupling agents and conditions are as described above. The amine of Formula (XVI) is commercially available.

The compound of Formula (XV) may be prepared according to Scheme 8, which uses methods analogous to those shown above in Scheme 1.

Scheme 8

The carboxylic acid of Formula (II) is reacted with commercially available L-4-fluorophenylalanine under the conditions provided for in Scheme 1. For example, methyl or tert-butyl protected L-4-fluorophenylalanine (XVII) is reacted with the compound of Formula (II) in DMF using a carbodiimide coupling agent. Alternatively, the activated succinimidyl ester of the compound of Formula (II) may first be prepared before subsequent reaction with L-4-fluorophenylalanine (XVII) in the presence of a base.

As a further aspect of the present invention, there is provided a novel process for the production of the compound of Formula (XV). As is discussed below, this process is efficient by virtue of avoiding racemisation of certain key intermediates and by permitting ready purification through use of reagents and products which are readily crystallisable. This process may be employed in the synthesis of 5-chloro-1H- pyrrolo[2,3-c]pyridine-2-carboxylic acid [1-(S)-(4-fluorobenzyl)-2-(4-hydroxypiperidin-1-yl)-2-oxoethyl]amide free base (compound of Formula (I)) and salt forms thereof, including the hydrochloride salt.

Thus, there is provided according to this aspect of the invention a process for preparing a compound of Formula (XV):

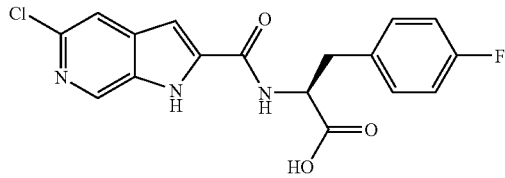

or an acid addition salt thereof,
which comprises reacting a compound of Formula (XVIII):

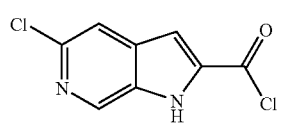

or an acid addition salt thereof, with a compound of Formula (XVII):

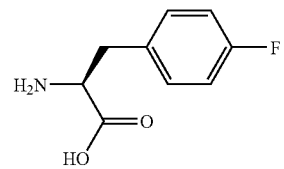

or a protected derivative thereof. The reaction is preferably conducted in a basic aqueous solution.

There is also provided according to the invention a process for preparing a compound of Formula (I):

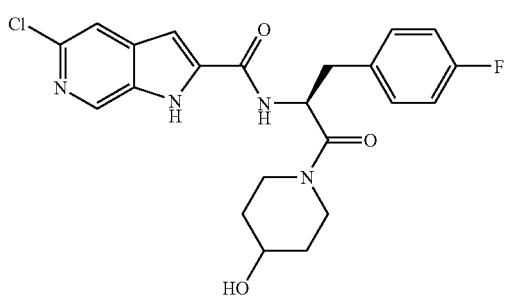

or an acid addition salt thereof, which comprises reacting a compound of Formula (XVIII):

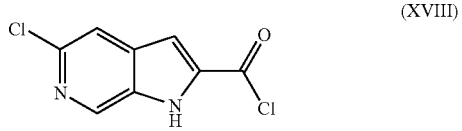 [SMILES: O=C(Cl)c1cc2cc(Cl)ncc2[nH]1]

or an acid addition salt thereof, with a compound of Formula (III):

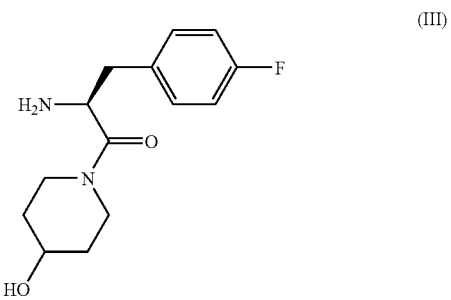 [SMILES: N[C@@H](Cc1ccc(F)cc1)C(=O)N1CCC(O)CC1]

or a protected derivative thereof. The process is preferably conducted in a basic aqueous solution.

According to the above mentioned processes, the compounds of Formula (XVIII) and (XVII) or (XVIII) and (III) are preferably reacted in aqueous solution under Schotten-Baumann conditions (see The Chemistry of Amides, Wiley, New York, 1970 pp 73-185) i.e. in the presence of base.

The basic aqueous solution may suitably contain an organic solvent immiscible with water e.g. THF.

The aqueous solution may suitably be made basic with hydroxide or carbonate e.g. sodium hydroxide and/or sodium carbonate.

For example, a suspension of N-5-chloropyrrolo[2,3-c]pyridin-2-carbonyl chloride or a salt thereof, preferably the hydrochloride salt in anhydrous THF can be added dropwise to an aqueous solution of (L)-4-fluorophenylalanine (XVII) containing $NaOH/Na_2CO_3$. Preferably a slight excess of (L)-4-fluorophenylalanine is used e.g. about 1.2 molar equivalents. Low temperature may be needed to prevent hydrolysis of the acyl chloride and racemization of the amino acid (even in acylated form). Preferably the reaction is carried at 0-5° C. since lower temperatures may result in stirring difficulties. The reaction mixture may be neutralized and the THF removed under vacuum. The product may be recovered as a precipitate after acidification of the solution (pH=1-2). The addition of EtOAc to the aqueous solution before acidification and filtration may provide a precipitate of better quality.

The compound of Formula (XV) may be purified by crystallization. A preferred solvent system for crystallization is 2M aqueous HCl solution and an alcoholic solvent e.g. methanol, ethanol or propanol, for example about a 2:1 mixture of 2M aqueous HCl solution and 2-propanol, from which the extended acid intermediate (compound of Formula (XV)) can be obtained as a crystalline hydrochloride salt.

A particular advantage of this process for preparing a compound of Formula (XV) is that it can be performed without the need to protect the amino acid (compound of Formula (XVII)). Also the process minimises the opportunity for racemisation of the chiral carbon.

In order to produce a compound of Formula (XVIII), 5-chloropyrrolo[2,3-c]pyridine-2-carboxylic acid may be treated with SOCl₂ in an inert solvent Reaction may be carried out in suspension, for example in toluene or acetonitrile, with 3-4 equivalent of SOCl₂ at reflux temperature. If the reaction is carried out in toluene, the acid chloride product (XVII) may be isolated by filtration. If the reaction is carried out in acetonitrile, the solvent may be removed under reduced pressure to recover the acid chloride.

In the preparation of a compound of Formula (I), the compound of Formula (XV) so produced may be reacted with a compound of Formula (XVI):

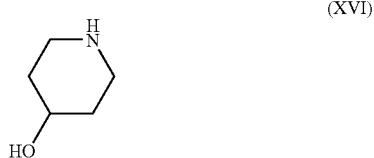

(XVI)

A range of methods for performing this coupling will be apparent to those skilled in the art. To enable the use of the isolated hydrochloride salt of the extended acid without liberation of base, suitable solvents include. Reduced levels of racemisation or side reactions are observed when the solvent used is EtOAc, propanol or THF. Suitable coupling agents include 2-chloro-4,6-dimethyl-1,3,5-triazine (CDMT) or (DMTMM). The reaction is performed in the presence of base, such as N-methylmorpholine or an excess of 4-hydroxypiperidine, preferably an excess of 4-hydroxypiperidine. Crude compound of Formula (I) may be isolated following the reaction.

The hydrochloride of the compound of Formula (I) may be purified by recrystallization, the recrystallisation conditions may determine the polymorphic form of the material which is obtained. Suitable solvent systems for crystallization are mixtures of 2M aqueous HCl solution and an alcoholic solvent e.g. methanol, ethanol or propanol, for example about a 2:1 mixture of 2M aqueous HCl solution and 2-propanol, and mixtures of an alcoholic solvent e.g. methanol, ethanol or propanol, and acetonitrile, for example about a 1:5 mixture of methanol and acetonitrile.

Thus according to a further aspect of the invention there is provided a process for the preparation of a hydrochloride of the compound of Formula (I) which comprises recrystallising a hydrochloride of the compound of Formula (I) from a mixture of aqueous HCl and an alcoholic solvent or a mixture of an alcoholic solvent and acetonitrile.

The invention also provides a hydrochloride of the compound of Formula (I) obtainable by such a recrystallisation method.

Reaction of the acid chloride of Formula (XVIII) with (XVII) according to the process of the invention to provide the compound of Formula (XV) is more efficient and leads to lower levels of racemisation of the chiral centre than the previous processes of Scheme 8 (for example, the succinimidyl ester of (II) in particular is difficult to handle and decomposes in water). The process of the invention may thereby enable higher yields of the compound of Formula (I) (and hence its hydrochloride salt to be obtained.

The acid chloride of the compound of Formula (XVIII) will advantageously be utilized in the form of a hydrochloride. Under such conditions the compound of Formula (XV) is produced as an acid addition salt with HCl, which may be crystallised and easily purified. The final product is therefore obtained at a high purity. In contrast, since the compound of Formula (III) prepared using in Scheme 3 is obtained an oil, the compound of Formula (I) prepared according to the Scheme 1 is generally contaminated with several by products having similar polarity and therefore this route is less favoured.

One of the advantages of the process of the invention defined above is that protection of labile functional groups in the intermediate compounds is unnecessary. However during the other processes described above labile functional groups in the intermediate compounds, e.g. hydroxy, carboxy and amino groups, may be protected. 5-Chloropyrrolo[2,3-c]pyridine-2-carboxylic acid may be protected in the 1-position e.g. with an arylmethyl, acyl, alkoxycarbonyl, sulfonyl or silyl group. The protecting groups may be removed at any stage in the synthesis of the compounds of Formula (I) or may be present on the final compound of Formula (I). A comprehensive discussion of the ways in which various labile functional groups may be protected and methods for cleaving the resulting protected derivatives is given in for example, Protective Groups in Organic Chemistry, T. W. Greene and P. G. M. Wuts, (1991) Wiley-Interscience, New York, $2^{nd}$ edition.

The novel process of the present invention may additionally be utilised in the production of analogues of the compound of Formula (I). In particular, analogues are contemplated wherein the 4-hydroxypiperidin-1-yl moiety is replaced with a moiety $R^3$ which is (i) a 4-8-membered nitrogen containing heterocyclyl group (linked via a ring nitrogen atom to the amino acid carbonyl), said heterocyclyl group being optionally substituted with 1-3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR⁷R⁸, —C(O)R⁹, $C_{1-4}$alkoxy$C_{0-4}$alkyl-, —COO$C_{0-4}$alkyl, —$C_{0-4}$alkylNHC(O)R⁹, —$C_{0-4}$alkylC(O)N(R¹⁰)₂, —$C_{1-4}$alkoxy$C_{1-4}$alkoxy, hydroxy$C_{0-4}$alkyl-, —NHSO₂R¹⁰, —SO₂($C_{1-4}$alkyl), —SO₂NR¹¹R¹², 5- to 6-membered heterocyclyl, phenyl$C_{0-2}$alkoxy, or phenyl$C_{0-2}$alkyl substituents, wherein phenyl is optionally substituted with 1-2 independent halogen, cyano, $C_{1-4}$alkyl, $C_{1-4}$alkoxy, —N($C_{0-4}$alkyl)($C_{0-4}$alkyl), —SO₂$C_{1-4}$alkyl, —SO₂N($C_{0-4}$alkyl)($C_{0-4}$alkyl), hydroxy, fluoromethyl, difluoromethyl, or trifluoromethyl substituents, or two bonds on a ring carbon of the heterocyclyl group optionally can form an oxo (=O) substituent; or (ii) a moiety —NR⁴(—$C_{0-4}$alkylR⁵) in which $R^4$ is $C_{0-3}$alkyl, —$C_{2-3}$alkyl-NR⁷R⁸, $C_{3-6}$cycloalkyl optionally substituted by hydroxy$C_{0-4}$alkyl- further optionally substituted by hydroxy, $C_{1-2}$alkoxy$C_{2-4}$alkyl-, or $C_{1-2}$alkyl-S(O)$_n$—$C_{2-3}$alkyl-;

n is 0, 1, or 2; and $R^5$ is hydrogen, hydroxy$C_{2-3}$alkyl-, $C_{1-2}$alkoxy$C_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO₂$C_{1-4}$alkyl, —SO₂N($C_{0-4}$alkyl)($C_{0-4}$alkyl), $C_{1-4}$alkoxycarbonyl or aryl($C_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-SO₂—, $C_{1-4}$alkyl, $C_{1-4}$alkoxy, hydroxy, —N($C_{0-4}$alkyl)($C_{0-4}$alkyl), hydroxy$C_{0-4}$alkyl-, or $C_{0-4}$alkylcarbamoyl-, provided that no quaternised nitrogen is included; or two bonds on a ring carbon of the heterocyclyl group optionally can form an oxo (=O) substituent;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle.

Such analogues may be prepared in the form of pharmaceutically acceptable salts thereof, e.g. the HCl salts.

Specific examples of nitrogen containing heterocyclyl groups which may replace the 4-hydroxypiperidin-1-yl moiety of the compound of Formula (I) include azetidin-1-yl, pyrrolidin-1-yl, piperidin-1-yl, 1,4-diazapan-1-yl, piperazin-1-yl, morpholin-4-yl, thiomorpholin-4-yl, 1,1-dioxo-thiomorpholin-4-yl, or thiazolidin-3-yl; which groups may be optionally substituted as described above. Preferred substituent groups for 4-hydroxypiperidin-1-yl replacement include —$C_{1-4}$alkoxy, hydroxy and oxo.

Even more preferably the replacement group is pyrrolidin-1-yl or piperidin-1-yl optionally substituted with hydroxyl, e.g. 3-(S)-hydroxypyrrolidin-1-yl.

Thus analogues of the compound of Formula (I) defined by Formula (IA):

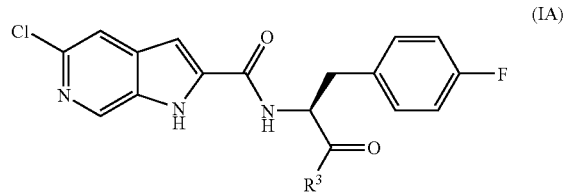

(IA)

in which $R^3$ is as defined above, may be prepared by reacting a compound of Formula (XVIII) with a compound of Formula (XVII) in an aqueous basic condition and then reacting the product of said reaction with an amine compound of Formula $R^3$—H. Suitable conditions include conditions similar to those described above for the reaction of a compound of Formula (XV) with a compound of Formula (XVI).

Any novel intermediates as defined above are also included within the scope of the invention.

The invention also provides 5-chloropyrrolo[2,3-c]pyridine-2-carbonyl chloride, or an acid addition salt thereof, in particular 5-chloropyrrolo[2,3-c]pyridine-2-carbonyl chloride hydrochloride.

All publications, including, but not limited to, patents and patent application cited in this specification, are herein incorporated by reference as if each individual publication were specifically and individually indicated to be incorporated by reference herein as fully set forth.

The invention will now be illustrated with reference to the following examples.

EXAMPLES

Analytical Methods

Thermogravimetric analysis was performed as follows: A sample of the material (ca. 4-5 mg) was heated in a platinum vessel using slow inert gas (nitrogen) flow with 5° C./min heating rate using Derivatograph C instrument.

X ray diffraction measurements were performed using Philips PW 3710/PW 1050 diffractometer (Cu Kα 40 kV, 35 mA).

Example 1

Figure 1:
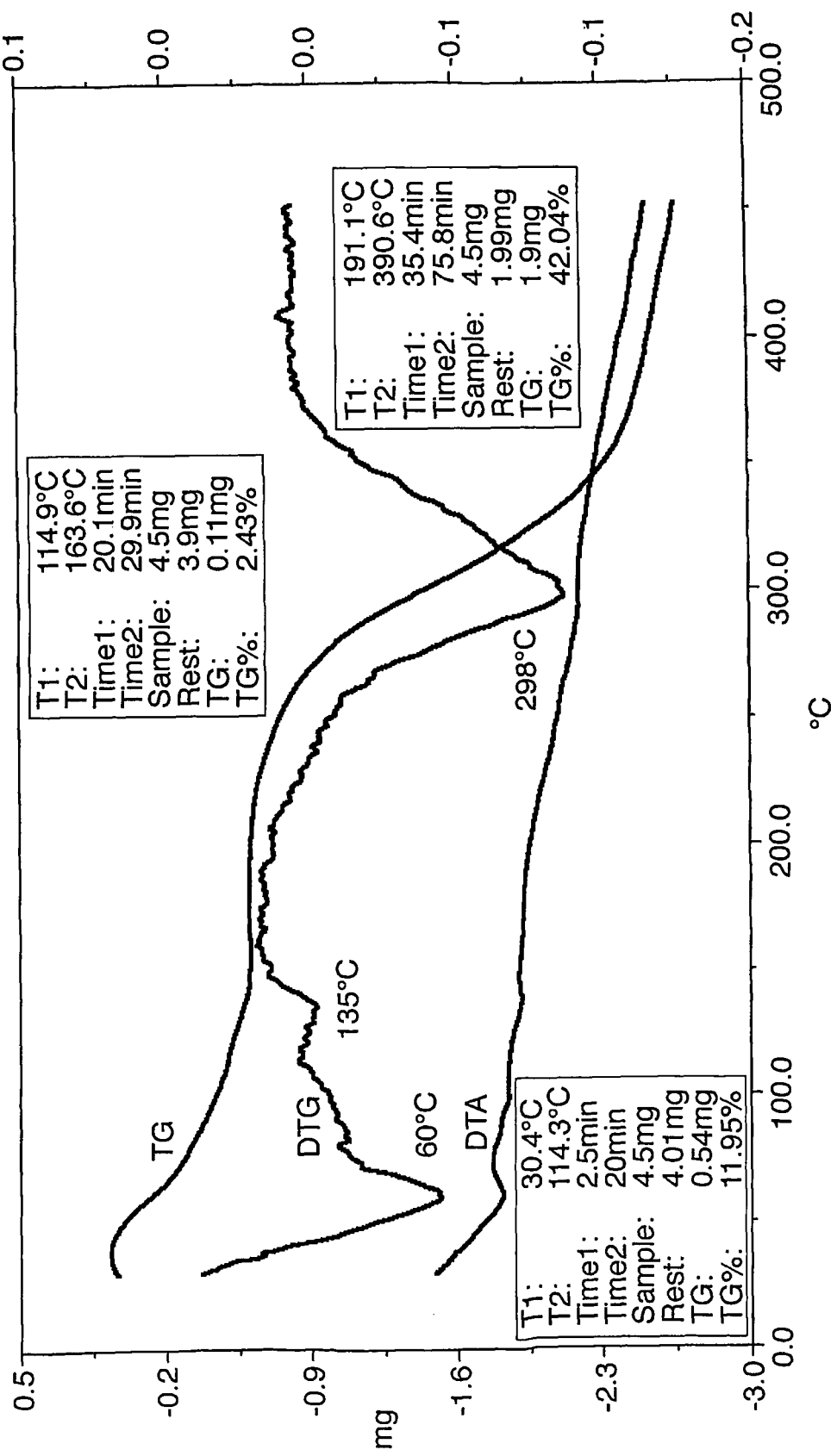
FIG. 1 shows thermogravimetric analysis of a hydrochloride salt of the invention (Example 1).

Synthesis of 5-chloropyrrolo[2,3-c]pyridine-2-carboxylic acid [1-(S)-4-fluorobenzyl)-2-(4-hydroxypiperidin-1-yl)-2-oxoethyl]amide hydrochloride (a) Preparation of 5-chloropyrrolo[2,3-c]pyridine-2-carbonyl chloride hydrochloride Method A: 5-Chloropyrrolo[2,3-c]pyridine-2-carboxylic acid (39.3 g, 0.20 mol) was suspended in acetonitrile and heated to reflux. Thionyl chloride (44 mL, 71.4 g, 0.60 mol) was added dropwise over 20 min at reflux temperature. The resulting suspension was heated at reflux for a further 3 h (TLC monitoring: n-butanol-acetic acid-water 4:1:1, UV visualised. Sample was prepared by quenching into methanolic $NH_3$ solution). The reaction mixture was evaporated to dryness under reduced pressure and the crude product used in the next step without further purification. Yield 49.3 g (98.0%).

Method B: A slurry of 5-chloro-1H-pyrrolo[2,3-c]-pyridin-2-carboxylic acid (300 g, 1.52 mol) in acetonitrile (3.75 L) was heated to reflux. Thionyl chloride (363 g, 3.052 mol, 223 mL) was added dropwise to the mixture and the reaction monitored by dc and hlpc. After completion of the reaction excess thionyl chloride and acetonitrile was distilled off under diminished pressure to obtain a thick slurry. Toluene (2 L) was added to the residue, and solvents evaporated under diminished pressure. The product was filtered off under nitrogen and washed with toluene (0.2 L) and hexane (0.2 L). The product was dried in vacuo at 45-50° C. over potassium hydroxide to obtain the title compound. Yield 368 g (96%). IR (KBr) 1750 cm$^{-1}$ (also 2436 br, 1981, 1869, 1631, 1588, 1529, 1447, 1389, 1340, 1289, 1203, 1140 and 1001 cm$^{-1}$).

(b) Preparation of N-(5-chloropyrrolo[2,3-c]pyridin-2-carbonyl)-L-4-fluorophenylalanine hydrochloride Method A: To a solution of NaOH (9.41 g, 0.235 mol, 1.2 eq) and $Na_2CO_3$ (62.3 g, 0.588 mol, 3.0 eq) in deionized water (240 mL) was added L-4-fluorophenylalanine (43.1 g, 0.235 mol, 1.2 eq) followed by THF (240 mL). The resulting solution was cooled to 0-5° C. and a suspension of 5-chloropyrrolo[2,3-c]pyridine-2-carbonyl chloride hydrochloride (49.3 g, 0.196 mol, 1.0 eq) in dry THF was added (~30 min). The reaction mixture was stirred at 0-5° C. for 15 min (HPLC monitoring, direct analysis of the sample). The temperature was maintained at 0-5° C. while the pH of the reaction mixture was adjusted to ~7 by the addition of conc. hydrochloric acid and THF was removed under reduced pressure. EtOAc (50 mL) was added to the remaining aqueous solution and the pH adjusted to 1-2 by the addition of conc. hydrochloric acid (~80 mL altogether). The resulting suspension was stirred for 30 min at 0-5° C. The precipitate was then filtered, washed with EtOAc (2×100 mL) and dried in vacuo at 40° C. Crude yield 67.6 g (86.6%). The crude product was crystallised from a mixture of 2M HCl (540 mL) and 2-propanol (270 mL). Yield 60.9 g (78.0%). $^1$H-NMR (DMSO): 13.02 (br s, 1H), 9.2 (d, 1H), 8.80 (s, 1H), 7.95 (s, 1H), 7.48 (s, 1H), 7.34 (dd, 2H), 6.96 (dd, 2H), 4.81 (m, 1H), 3.29 (dd, 1H), 3.16 (dd, 1H).

Method B: To a solution of NaOH (73.0 g, 1.82 mol) and $Na_2CO_3$ (486 g, 4.58 mol) in deionized water (1.90 L) was added L-4-fluorophenylalanine (336 g, 1.82 mol) followed by THF (2.80 L). The resulting solution was cooled to 0-5° C. and a suspension of 5-chloropyrrolo[2,3-c]pyridine-2-carbonyl chloride hydrochloride (383 g, 1.52 mol) in dry THF was added (~30 min). The reaction mixture was stirred at 0-5° C. for 30 min (HPLC monitoring, direct analysis of the sample). The temperature was maintained at 0-5° C. while the pH of the reaction mixture was adjusted to ~7 by the addition of conc. hydrochloric acid (230 mL) and THF was removed under reduced pressure. EtOAc (3.0 L) was added to the residue and the pH adjusted to 1-2 by the addition of conc. hydrochloric acid (0.6 L). The resulting slurry was stirred for 30 min at 0-5° C. The precipitate was then filtered, washed with EtOAc (2×500 mL) and dried in vacuo at 40-50° C. (95% purity by HPLC).

(c) Preparation of 5-chloropyrrolo[2,3-c]pyridine-2-carboxylic acid [1-(S)-fluorobenzyl)-2-(4-hydroxypiperidin-1-yl)-2-oxoethyl]amide hydrochloride Method A: N-(5-Chloropyrrolo[2,3-c]pyridine-2-carbonyl)-L-4-fluorophenylalanine hydrochloride (60.9 g, 0.153 mol) was suspended in dry THF (460 mL) and the mixture was stirred at room temperature. 4-Hydroxypiperidine (35.7 g, 0.353 mol) was added portionwise (slight exotherm) and the mixture stirred at room temperature for 10 min. 4-(4,6-Dimethoxy-1,3,5-triazin-2-yl)-4-methylmorpholinium chloride (51.2 g, 0.185 mol, prepared according to the method of Kunishima et al, *Tetrahedron Letters*, 1999, 40, 5327-5330) was then added in one portion. The reaction mixture was stirred at room temperature for 1 h (HPLC monitoring, direct sample analysis). The solvent was removed under reduced pressure and the residue partitioned between EtOAc (500 mL) and saturated $Na_2CO_3$ solution (500 mL)-water (600 mL) mixture. The organic layer was separated and the aqueous layer extracted with EtOAc (2×150 mL), the combined organic layers was washed with brine, dried over $Na_2SO_4$ and evaporated. Crude yield (base) 70.9 g. The crude product was crystallised from a mixture of 2M HCl (420 mL) and 2-propanol (210 mL) to give 35.1 g (47.7%) of a light yellow crystalline material (water content 13.2% and >98% optical purity). A second crystallisation from the same mixture gave 21.4 g (29.1%) pure product with >99% optical purity. $^1$H-NMR (DMSO): 13.2 (br s, 1H), 9.24 (dd, 1H), 8.90 (s, 1H), 7.95 (s, 1H), 7.50 (s, 1H), 7.28 (dd, 2H), 6.96 (dd, 2H), 5.25 (qa, 1H), 3.12 (m, 1H), 1.85-1.115 (m, 9H).

Method B: N-(5 Chloropyrrolo[2,3-c]pyridine-2-carbonyl)-L-4-fluorophenylalanine hydrochloride (450 g, 1.13 mol) was suspended in dry THF (3.40 L) and the mixture cooled to 20-25° C. 4-Hydroxypiperidine (264 g, 2.60 mol) was added portionwise (slight exotherm) and the mixture stirred at 20-25° C. for 5-10 min. 4-(4,6-Dimethoxy-1,3,5-triazin-2-yl)methylmorpholinium chloride (380 g, 1.37 mol, prepared according to the method of Kunishima et al, *Tetrahedron Letters*, 1999, 40, 5327-5330) was then added. The reaction mixture was stirred at 20-25° C. (HPLC monitoring, direct sample analysis). The reaction mixture was poured into a stirred solution of sodium carbonate (700 g) in deionised water (7 L), EtOAc (500 mL) was added and the mixture stirred for 10 min. The organic layer was separated and the aqueous layer extracted with EtOAc (1×1 L and 1×500 mL), the combined organic layers was washed with brine (2.0 L) and dried over $Na_2SO_4$ (70 g) and activated carbon (15 g) overnight before the solvent was evaporated. The crude product was dissolved in methanol (2.0 L) and 2M HCl (2.50 L), Celite (10 g) and activated carbon (10 g) added. The resulting slurry was stirred for 30 min. The mixture was filtered and the methanol removed under reduced pressure. The crystal slurry was cooled overnight to 4-5° C., filtered, washed with 2M HCl (0.20 L) and dried in vacuo at 50° C. The product was recrystallised from a mixture of 2M HCl (2.10 L) and 2-propanol (0.9 L) and the product dried over KOH in vacuo at 50° C.

Analytical Methods

Thermal stability data on the product of Example 1 were obtained by the thermogravimetric method described above. The resultant trace is shown in FIG. 1. The substance appeared to be stable below 190° C. The transition at around 40° C. corresponds to vaporization of possible solvent or water.

Figure 2:
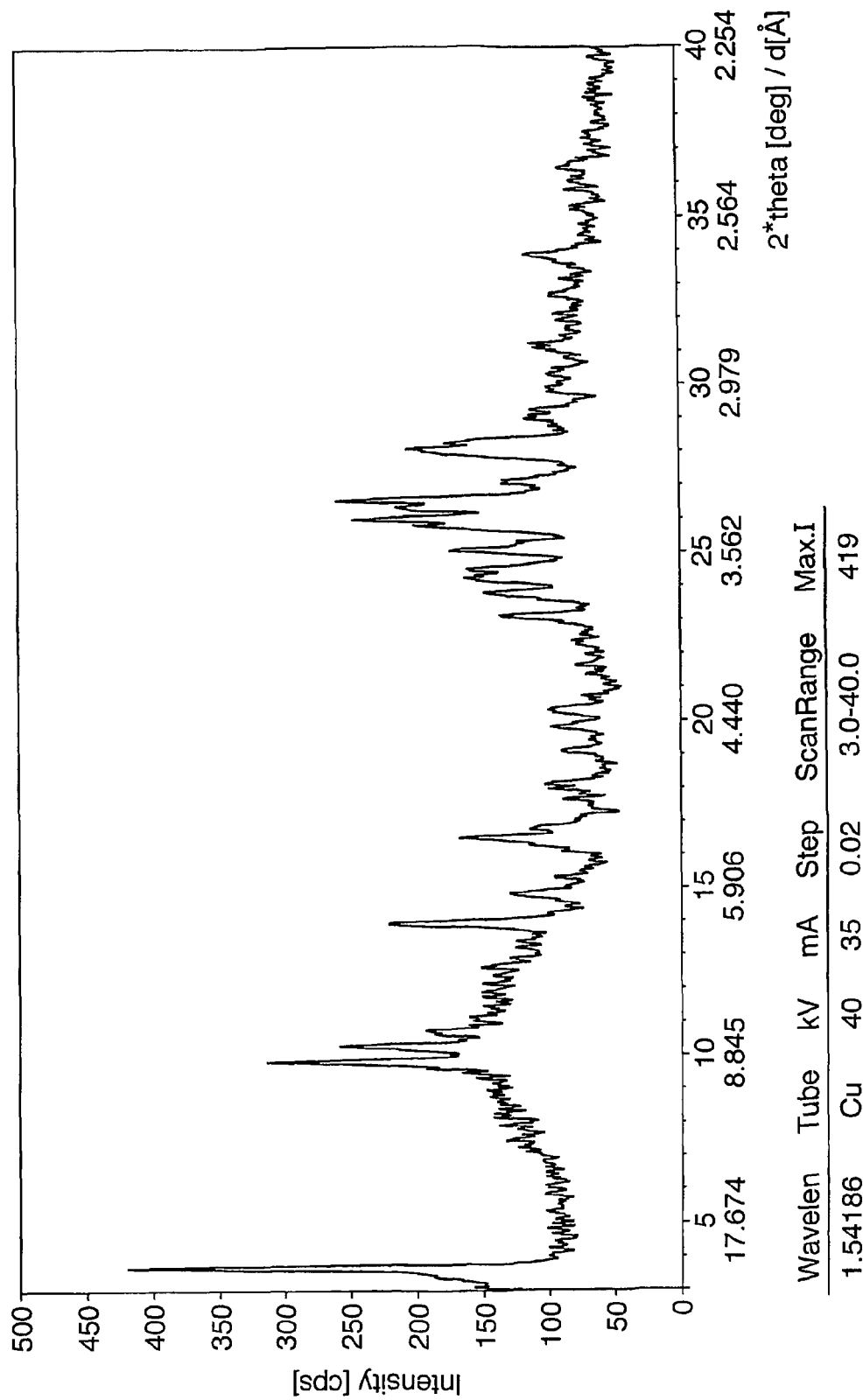
FIGS. 2-5 show X-ray diffraction patterns for a hydrochloride salt of the invention at different states of hydration (Example 1).

The properties of the product of Example 1 were studied using X-ray scattering following the methods described above. Analysis was performed at 4 stages of the purification process:

FIG. 2 shows the trace corresponding to crude product obtained in wet form after washing.

Figure 3:
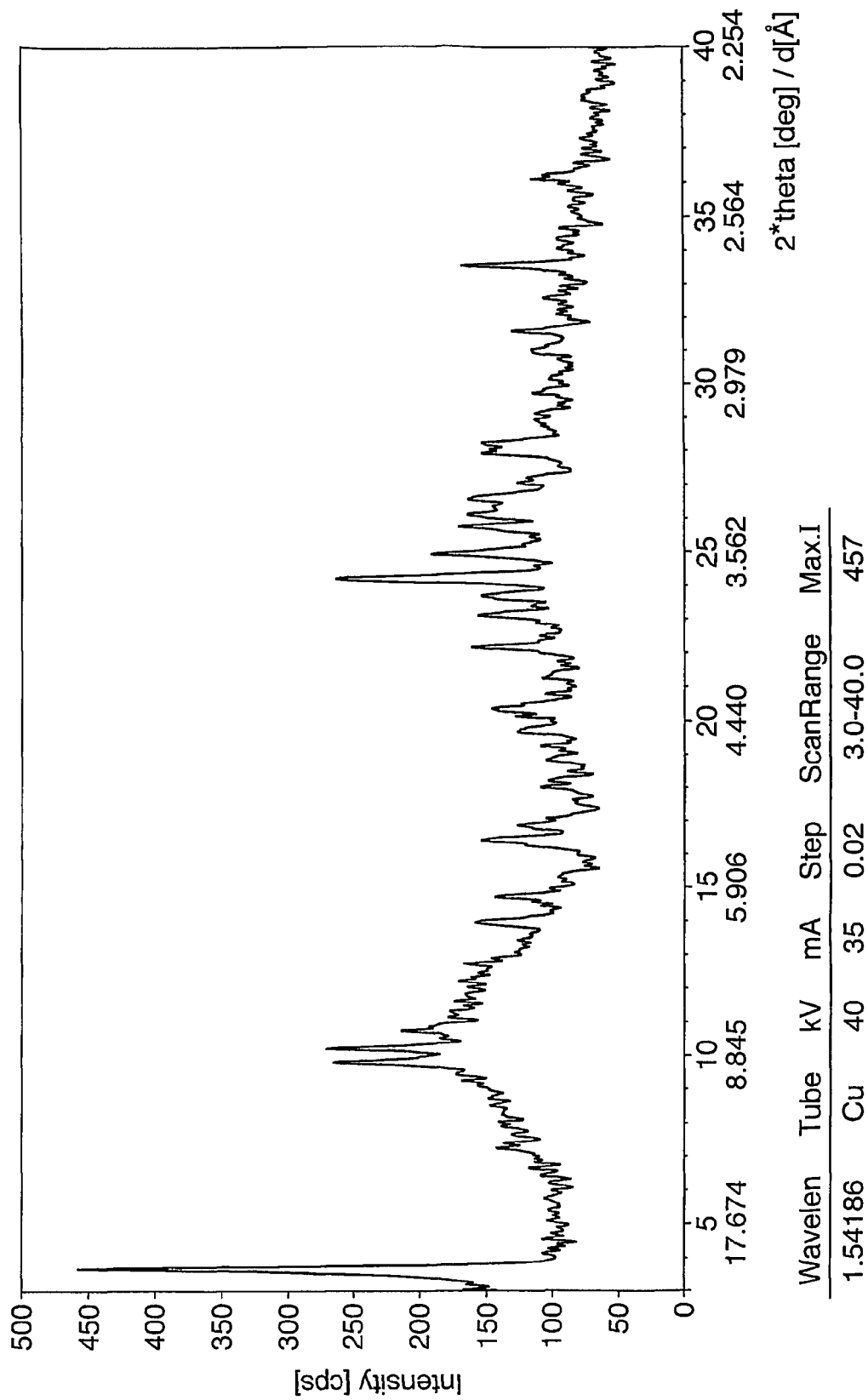

FIG. 3 shows the trace corresponding to crude product obtained after washing with EtOAc.

Figure 4:
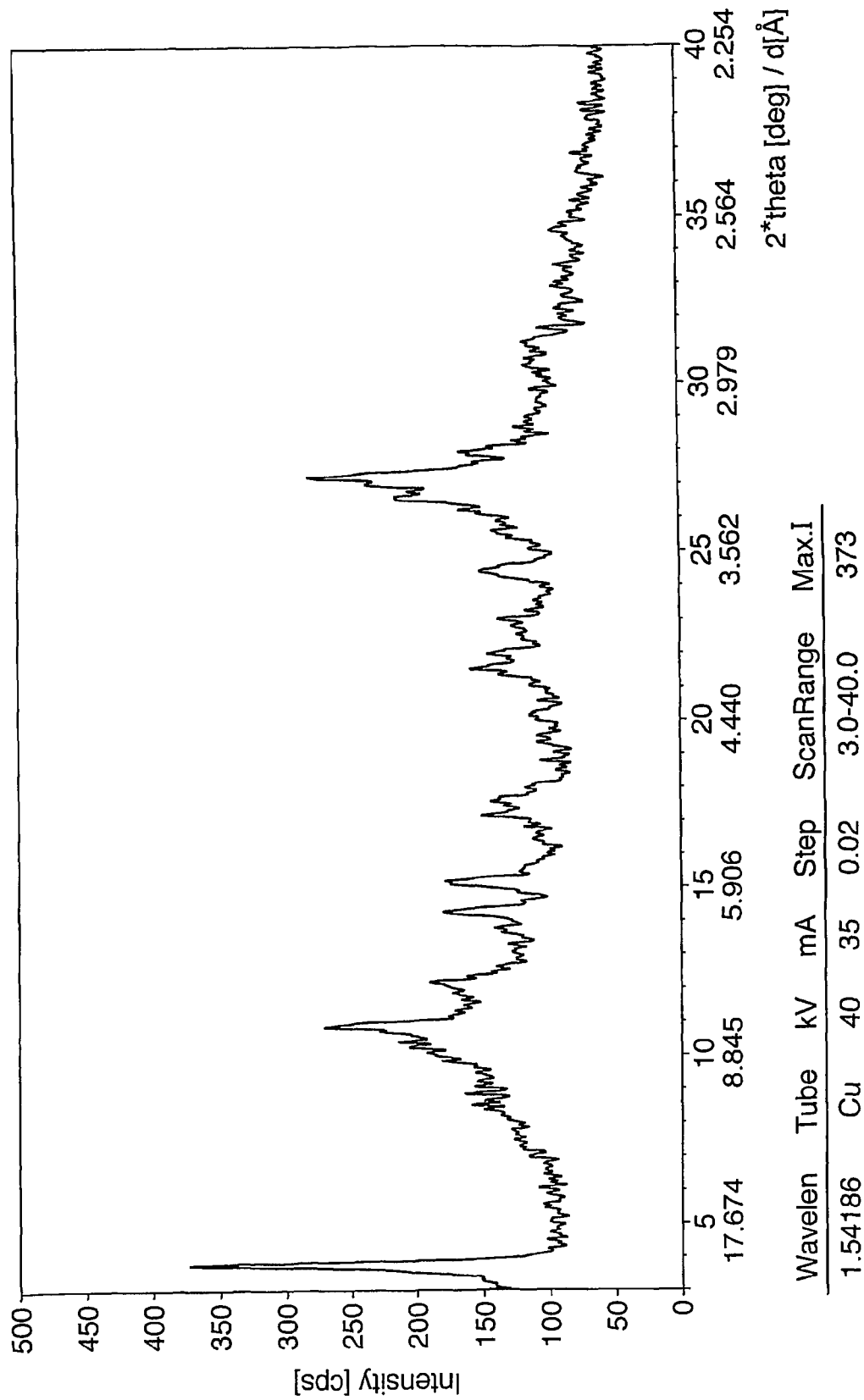

FIG. 4 shows the trace corresponding to final product after drying. The wet product (50-60% volatile content) was dried at 30° C. (8 h) then the temperature was increased gradually to 50° C. over 10 h and the drying continued at this temperature for 24 h.

Figure 5:
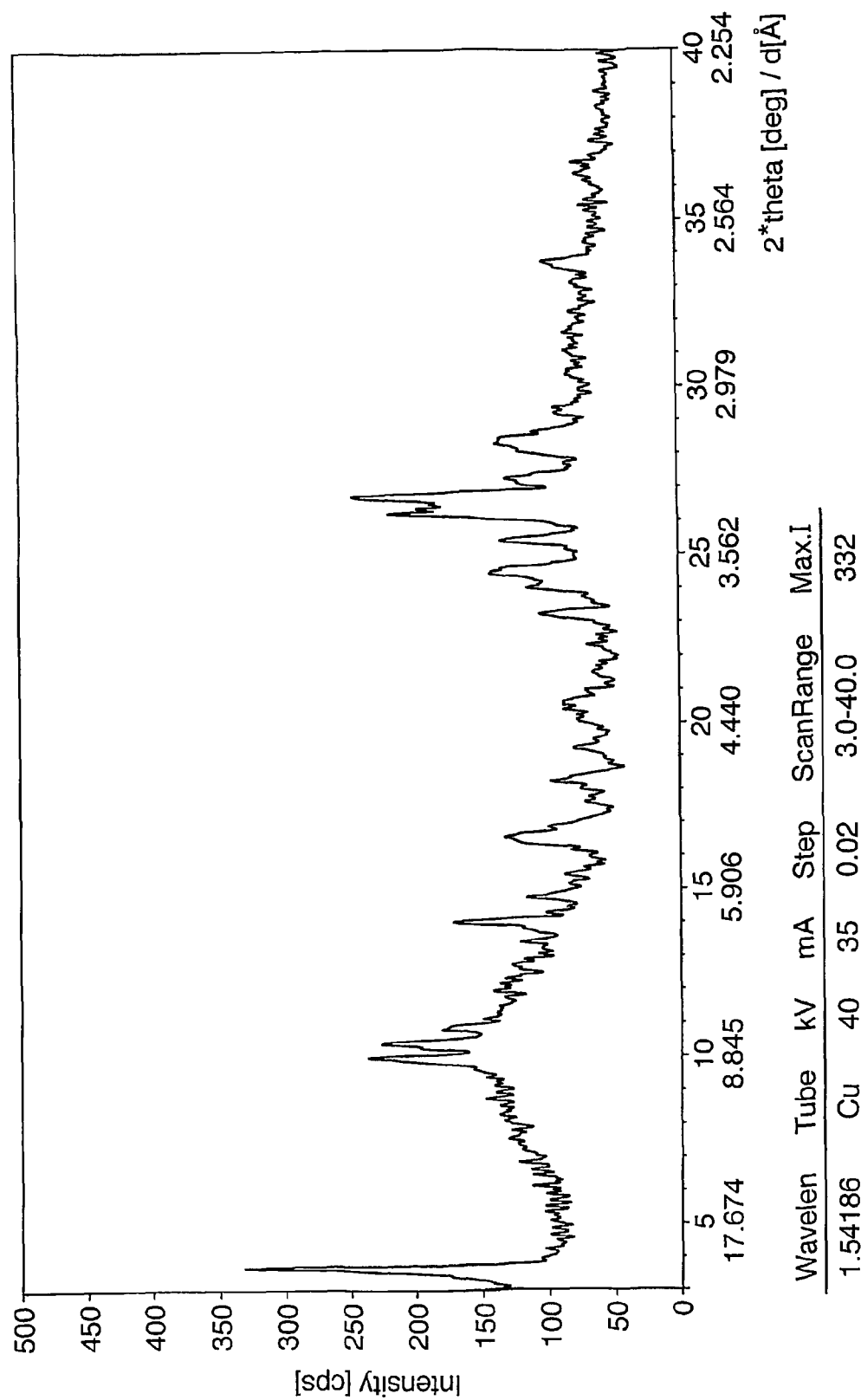

FIG. 5 shows the trace corresponding to final product after drying as described above then storing under air above wet silica gel for 12 h resulting in the production of material with equilibrium moisture content and substantially crystalline structure.

Example 2

Recrystallisation of 5-chloropyrrolo[2,3-c]pyridine-2-carboxylic acid [1-(S) fluorobenzyl)-2-(4-hydroxypiperidin-1-yl)-2-oxoethyl]amide hydrochloride from methanol:acetonitrile 5-Chloropyrrolo[2,3-c]pyridine-2-carboxylic acid [1-(S)-4-fluorobenzyl)-2-(4-hydroxypiperidin-1-yl)-2-oxoethyl] amide hydrochloride (10 g, material obtained according to Example 1 but without recrystallisation) was dissolved in methanol (20 mL) at 50° C. and under continuous stirring acetonitrile (100 mL) was added. The product stared to precipitate at the end of the addition of acetonitrile. The mixture was warmed to 40° C. to get homogenous solution. After addition of the acetonitrile the suspension was cooled to 0° C. under continuous stirring. The product was crystallized for 12 h at 0° C. The precipitate was filtered on a sintered glass filter. The filter cake was washed with of acetonitrile (10 mL) and the product was dried at 45° C. in vacuum yielding product with >99% optical purity. Mp 77-78° C. Water content 4.5-5.5% w/w.

Analytical Methods

Figure 6:
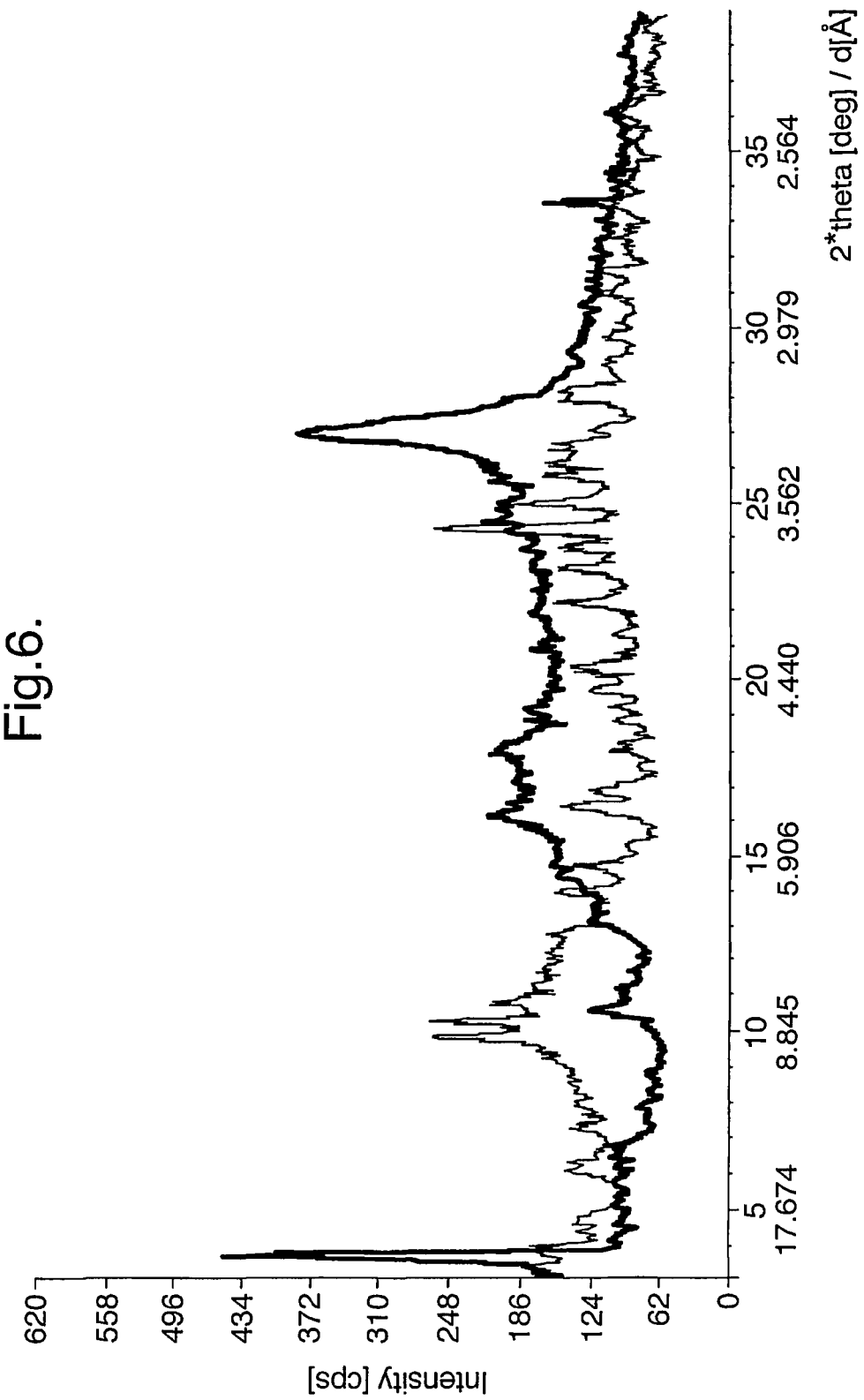
FIG. 6 show X-ray diffraction pattern for a hydrochloride salt of the invention (Example 2) overlayed with that of Example 1.

The properties of the product of Example 2 were studied using X-ray scattering following the methods described above. FIG. 6 shows the trace corresponding to this product overlayed with that obtained for the material of Example 1.

In Vitro GP Activity

Materials

α-D-Glucose-1-phosphate (disodium salt), Glycogen, D-Glucose, Malachite Green Hydrochloride, Ammonium Molybdate tetrahydrate, BSA, HEPES and rabbit muscle phosphorylase a (P1261) were purchased from Sigma. All other reagents were analytical grade.

Method

Glycogen Phosphorylase Assay In Vitro:

An assay for glycogen phosphorylase activity in the reverse direction was developed based on the method described by Engers et al., *Can. J. Biochem.*, 1970, 48, 746-754]. Rabbit muscle glycogen phosphorylase a (Sigma) was reconstituted at a stock concentration of 100 μg/mL in 25 mM Tris/HCl. The pH was measured in a 96-well plate in a final volume of 100 μL containing 50 mM Hepes pH 7.2, 7.5 mM glucose, 0.5 mM glucose-1-phosphate and 1 mg/mL glycogen. After incubation at 30° C. for 30 min, the inorganic phosphate released from glucose-1-phosphate was measured by the addition of 150 μL of malachite green/molybdate solution prepared as follows: 5 mL of 4.2% ammonium molybdate in 4N HCl, 15 mL of 0.045% malachite green, 50 μL of Tween 20. Following a 30 min incubation at room temperature, the absorbance was measured at 620 nm. For $IC_{50}$ determination, 10 μL of a serial dilution of compound (100 μM to 0.004 μM) in DMSO was added to each reaction in duplicate with the equivalent concentration of DMSO added to the control uninhibited reaction. Dose response curves were then obtained by plotting % inhibition versus $\log_{10}$ compound concentration. $IC_{50}$ is defined as the concentration of compound achieving 50% inhibition under the assay conditions described. The compound of Formula (I) has an $IC_{50}$ of <1 mM.

The invention claimed is:

1. A compound which is a hydrochloride salt of the compound of Formula (I):

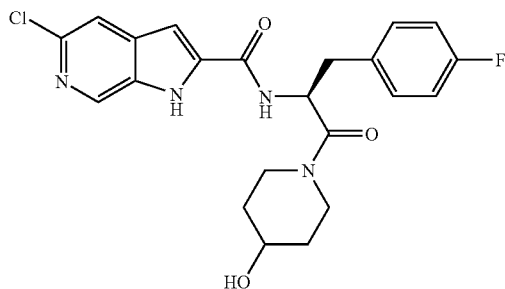 [SMILES: O=C(N[C@@H](Cc1ccc(F)cc1)C(=O)N1CCC(O)CC1)c1cc2cc(Cl)ncc2[nH]1]

wherein the compound is in crystalline form and further wherein said compound exhibits a melting point of about 77-78° C. and a water content of about 4.5-5.5% w/w.

2. A pharmaceutical composition comprising a compound according to claim 1 in admixture with a pharmaceutically acceptable carrier.

3. A pharmaceutical composition according to claim 2 presented as a discrete unit suitable for oral administration.

4. A pharmaceutical composition according to claim 2 presented as a solid dosage form.

5. A pharmaceutical composition according to claim 1 in the form of a tablet, cachet or capsule.

6. A method of therapeutic treatment of hyperglycemia or diabetes, which comprises a step of administering a compound according to claim 1 to a subject in need thereof.

7. A method of therapeutic treatment of diabetes in a human demonstrating pre-diabetic hyperglycemia or impaired glucose tolerance, which comprises a step of administering a compound according to claim 1.

8. A method of therapeutic treatment of hypercholesterolemia, hyperinsulinemia, hyperlipidemia, atherosclerosis or myocardial ischemia, which comprises a step of administering a compound according to claim 1 to a subject in need thereof.

9. A compound of Formula (XVIII):

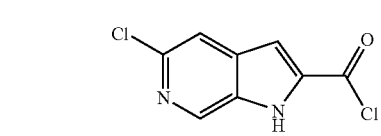

in the form of its HCl acid addition salt.

* * * * *

UNITED STATES PATENT AND TRADEMARK OFFICE
CERTIFICATE OF CORRECTION

| | | |
|---|---|---|
| PATENT NO. | : 8,664,397 B2 | Page 1 of 1 |
| APPLICATION NO. | : 11/792183 | |
| DATED | : March 4, 2014 | |
| INVENTOR(S) | : Repasi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1240 days.

Signed and Sealed this
Eighth Day of September, 2015

Michelle K. Lee
*Director of the United States Patent and Trademark Office*